(12) United States Patent
Lin et al.

(10) Patent No.: US 12,310,990 B2
(45) Date of Patent: May 27, 2025

(54) METHOD FOR TREATING ARTHRITIS BY USING STEM CELL PREPARATION AND METHOD FOR PREPARING STEM CELL PREPARATION

(71) Applicant: GWO XI STEM CELL APPLIED TECHNOLOGY CO., LTD., Zhubei (TW)

(72) Inventors: Feng-Huei Lin, Zhubei (TW); Che-Yung Kuan, Zhubei (TW); Yu-Ying Lin, Zhubei (TW); Ching-Yun Chen, Zhubei (TW); Zhi-Yu Chen, Zhubei (TW); I-Hsuan Yang, Zhubei (TW); Ming-Hsi Chuang, Zhubei (TW); Po-Cheng Lin, Zhubei (TW); Chia-Hsin Lee, Zhubei (TW); Kai-Ling Zhang, Zhubei (TW); Pei-Syuan Chao, Zhubei (TW); Wan-Sin Syu, Zhubei (TW); Chun-Hung Chen, Zhubei (TW); Ting-Ju Wang, Zhubei (TW)

(73) Assignee: GWO XI STEM CELL APPLIED TECHNOLOGY CO., LTD., Jhubei (TW)

( * ) Notice: Subject to any disclaimer, the term of this patent is extended or adjusted under 35 U.S.C. 154(b) by 449 days.

(21) Appl. No.: 17/470,487

(22) Filed: Sep. 9, 2021

(65) Prior Publication Data
US 2023/0201266 A1     Jun. 29, 2023

(30) Foreign Application Priority Data
Jul. 15, 2021 (TW) ................. 110126154

(51) Int. Cl.
*A61K 35/28* (2015.01)
*A61P 19/02* (2006.01)
*C12N 5/00* (2006.01)
*C12N 5/0775* (2010.01)

(52) U.S. Cl.
CPC .............. *A61K 35/28* (2013.01); *A61P 19/02* (2018.01); *C12N 5/0062* (2013.01); *C12N 5/0667* (2013.01); *C12N 2513/00* (2013.01); *C12N 2533/30* (2013.01)

(58) Field of Classification Search
None
See application file for complete search history.

(56) References Cited

U.S. PATENT DOCUMENTS

2011/0171726 A1* 7/2011 Kang ................... C12N 5/0667
435/325

OTHER PUBLICATIONS

Jiang et al (Theranostics 9:6587-6600, published Aug. 21, 2019) (Year: 2019).*
Hyunchul Jo et al (Stem Cells 32:1254-1266, 2014) (Year: 2014).*
Bartosh et al (PNAS 107:13724-13729, 2010) (Year: 2010).*
Chahal et al (Stem Cells Translational Medicine 8:746-757, 2019) (Year: 2019).*
Zhou et al (Asian Journal of Andrology 19:91-97, 2017) (Year: 2017).*
Huang et al (Cell Transplantation 22:701-709, 2013) (Year: 2013).*
Song et al (Adv Healthcare Mater 9:1901612, 2020) (Year: 2020).*
Egger et al (Bioengineering 5(48):5020048, 2018) (Year: 2018).*

* cited by examiner

*Primary Examiner* — Craig D Ricci
(74) *Attorney, Agent, or Firm* — Muncy, Geissler, Olds & Lowe, P.C.

(57) ABSTRACT

The present disclosure provides a method for treating arthritis by using a stem cell preparation. The stem cell preparation of the present disclosure can effectively delay cartilage degeneration caused by arthritis, and it is confirmed by whole blood analysis and blood biochemical analysis that the stem cell preparation in the form of three-dimensional stem cell spheres provides a safe treatment for arthritis. The present disclosure also provides a method for preparing the stem cell preparation.

6 Claims, 8 Drawing Sheets
Specification includes a Sequence Listing.

SEQUENCE LISTING

```
<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
ggttgagccg tggagggaa at                                          22

<210> SEQ ID NO 2
<211> LENGTH: 21
<212> TYPE: DNA
<213> ORGANISM: Artificial Sequence
<220> FEATURE:
<223> OTHER INFORMATION: Synthetic Primer

<400> SEQUENCE: 2
tgccatgaat ggtggccagg t                                          21

<210> SEQ ID NO 3
<211> LENGTH: 19
<212> TYPE: DNA
<213> ORGANISM: Artificial Sequence
<220> FEATURE:
<223> OTHER INFORMATION: Synthetic Primer

<400> SEQUENCE: 3
cgctgtcttc tagcgttgc                                             19

<210> SEQ ID NO 4
<211> LENGTH: 19
<212> TYPE: DNA
<213> ORGANISM: Artificial Sequence
<220> FEATURE:
<223> OTHER INFORMATION: Synthetic Primer

<400> SEQUENCE: 4
tcgtcagagg gctgggatg                                             19

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5
ggcaagctct ggagacttct g                                          21

<210> SEQ ID NO 6
<211> LENGTH: 19
<212> TYPE: DNA
<213> ORGANISM: Artificial Sequence
<220> FEATURE:
```

<223> OTHER INFORMATION: Synthetic Primer

<400> SEQUENCE: 6
ctgcagcgcc ttgaagatg                                              19

<210> SEQ ID NO 7
<211> LENGTH: 17
<212> TYPE: DNA
<213> ORGANISM: Artificial Sequence
<220> FEATURE:
<223> OTHER INFORMATION: Synthetic Primer

<400> SEQUENCE: 7
tcgaggacag cgaggcc                                                17

<210> SEQ ID NO 8
<211> LENGTH: 22
<212> TYPE: DNA
<213> ORGANISM: Artificial Sequence
<220> FEATURE:
<223> OTHER INFORMATION: Synthetic Primer

<400> SEQUENCE: 8
tcgagggtgt agcgtgtaga ga                                          22

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
acaatgacgg agtccctgac                                             20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
tctgcatcaa agtcgtcctg                                             20

<210> SEQ ID NO 11
<211> LENGTH: 19
<212> TYPE: DNA
<213> ORGANISM: Artificial Sequence
<220> FEATURE:
<223> OTHER INFORMATION: Synthetic Primer

<400> SEQUENCE: 11
gagacagcat gacgccgag                                              19

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
gcggatgctc tcaatctggt                                             20

```
<210> SEQ ID NO 13
<211> LENGTH: 17
<212> TYPE: DNA
<213> ORGANISM: Artificial Sequence
<220> FEATURE:
<223> OTHER INFORMATION: Synthetic Primer

<400> SEQUENCE: 13
tgcccccgac cgtctac                                                    17

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
atgcggttcc agcctatctg                                                 20
```

METHOD FOR TREATING ARTHRITIS BY USING STEM CELL PREPARATION AND METHOD FOR PREPARING STEM CELL PREPARATION

The instant application contains a Sequence Listing which has been submitted electronically in the ASCII text file and is hereby incorporated by reference in its entirety. The ASCII text file is a sequence listing entitled "2021-10-20-Sequence-Listing" created on Oct. 20, 2021 and having a size of 2,969 bytes in compliance of 37 CFR 1.821.

CROSS-REFERENCE TO RELATED APPLICATION

This application claims priority of Taiwan patent application No. 110126154, filed on Jul. 15, 2021, the content of which is incorporated herein in its entirety by reference.

BACKGROUND OF THE INVENTION

1. Field of the Invention

The present invention relates to a method for treating arthritis by using a stem cell preparation, and a method for preparing the stem cell preparation.

2. The Prior Art

Arthritis is one of the most common chronic diseases in the world. It is mainly caused by the deterioration of the cartilage of the joints or inflammation of the connective tissue, which causes joint pain and interferes with the normal movement of the joints. There are more than one hundred types in total. There are many causes of arthritis, and joint damage is also different. There are approximately 355 million arthritis patients in the world, of which more than 100 million are in China. In the United States, one in five people suffers from arthritis pain and discomfort; in Asia, one in six people suffers from the disease at some point in their lives. Arthritis is not a disease unique to the elderly, it can affect all ages, including children.

Arthritis can occur in the back, neck, knees, shoulder joints, hands, hip joints, and ankles. Most arthritis is related to human aging. People over sixty years old would suffer from some types of arthritis but young people would also suffer from arthritis. There are more than one hundred types of osteoarthritis (OA), rheumatoid, rheumatic and septic arthritis, traumatic osteoarthritis, and autoimmune arthritis, and ankylosing arthritis is also a type of arthritis.

Osteoarthritis, also known as degenerative arthritis, is a symptom of diarthrosis failure. The main symptoms are degeneration of articular cartilage and friction between bones, resulting in joint pain, tenderness, stiffness, locking, joint effusion, decreased joint mobility, loss of joint space, osteophyte formation, cyst formation, joint deformation, and in severe cases may lead to disability. With the advent of an aging society, various chronic diseases have emerged one by one, and osteoarthritis has also become a serious problem. Osteoarthritis is a common joint disease in the world. 30% of the population in the United States is affected. The World Health Organization (WHO) has set the theme of bone and joint diseases from 2000 to 2010 since 2000. In the past ten years, October 12th is designated as "World Arthritis Day" every year. At present, nearly 400 million people in the world are suffering from arthritis. According to the Global-Data market report, the osteoarthritis market continues to grow from USD 1.6 billion in 2016 to 3.5 billion in 2026, with a compound annual growth rate (CAGR) of 8.1% from 2016 to 2026. According to the 2017 National Health Insurance Medical Statistics Annual Report, the expenditure on outpatient and hospitalization for osteoarthritis is nearly NT$5 billion, and the market potential is considerable. The current treatment for osteoarthritis is mainly pain management and cannot prevent further degeneration. When the pain seriously interferes with normal life and obvious functional deterioration, surgical operations such as total knee replacement (TKR) will be performed. Therefore, preventing the continuous degeneration of bones and joints and regenerating cartilage tissue is the ultimate goal of treating osteoarthritis.

Current treatments for osteoarthritis include: arch pad correction, functional knee pads, rehabilitation medicine electrotherapy, glucosamine, chondroitin, non-steroidal anti-inflammatory drugs (NSAID), intra-articular injection of corticosteroids, intra-articular injection of hyaluronic acid (HA), injection of platelet rich plasma (PRP), autologous chondrocyte implantation (ACI), partial knee replacement, TKR, and the like. According to the treatment guidelines listed in the second edition of the osteoarthritis treatment guidelines issued by the American Academy of Orthopaedic Surgeons (AAOS), it is recommended to treat with non-steroidal anti-inflammatory drugs. When the drug treatment fails, surgical operation is recommended. Although joint replacement can be used for 10 to 30 years, most patients with osteoarthritis have low acceptance of surgery, and the current treatment for osteoarthritis is mainly pain management, and it cannot prevent further degeneration.

In order to solve the above-mentioned problems, those skilled in the art urgently need to develop novel and more effective medicaments for treating arthritis without causing the aforementioned shortcomings for the benefit of a large group of people in need thereof.

SUMMARY OF THE INVENTION

A primary objective of the present invention is to provide a method for treating arthritis, comprising administering to a subject in need thereof a pharmaceutical composition comprising an effective amount of a stem cell preparation, wherein the stem cell preparation comprises a stem cell sphere.

According to an embodiment of the present invention, the arthritis is degenerative arthritis.

According to an embodiment of the present invention, the stem cell sphere has a size greater than 0 μm and less than 50 μm.

According to an embodiment of the present invention, the stem cell sphere comprises a stem cell selected from the group consisting of: an adipose-derived stem cell (ADSC), an umbilical cord mesenchymal stem cell, and a combination thereof.

According to an embodiment of the present invention, the adipose-derived stem cell is a primary human adipose-derived stem cell.

According to an embodiment of the present invention, the stem cell sphere is prepared by seeding the primary human adipose-derived stem cell on a scaffold to form a cell scaffold copolymer, followed by sequentially performing a static cultivation and a dynamic cultivation on the cell scaffold copolymer.

Another objective of the present invention is to provide a method for preparing a stem cell preparation, comprising: seeding a primary human adipose-derived stem cell on a scaffold to form a cell scaffold copolymer, followed by sequentially performing a static cultivation and a dynamic cultivation on the cell scaffold copolymer.

According to an embodiment of the present invention, the primary human adipose-derived stem cell is seeded on the scaffold at a concentration of at least $1\times10^6$ cells/scaffold.

According to an embodiment of the present invention, the time of the static cultivation is 2 days.

According to an embodiment of the present invention, the time of the dynamic cultivation is 14 days.

According to an embodiment of the present invention, the stem cell sphere has a concentration of at least $1\times10^6$ cells/50 µL.

According to an embodiment of the present invention, the stem cell sphere expresses a surface marker selected from the group consisting of: CD73, CD90, CD105, and a combination thereof.

According to an embodiment of the present invention, the stem cell sphere expresses a cartilage-related gene selected from the group consisting of: a transforming growth factor-β1 (TGF-β1) gene, a bone morphogenetic protein-2 (BMP-2) gene, a Sox9 gene, an Aggrecan gene, a cartilage oligomeric matrix protein (COMP) gene, a collagen type II alpha 1 chain (Col2a1) gene, and a combination thereof.

According to an embodiment of the present invention, the pharmaceutical composition is in a dosage form for parenteral administration.

In summary, the effect of the stem cell preparation of the present invention is that treating rats with arthritis induced by mono-iodoacetate (MIA), using a gait analyzer and hematoxylin & eosin (H&E) staining and toluidine blue staining for treatment evaluation, and evaluating the feasibility of applying the stem cell preparation to the treatment of arthritis. It was found that the stem cell preparation of the present invention can effectively delay arthritis (especially degenerative arthritis) caused by cartilage degradation, and whole blood analysis and blood biochemical analysis confirmed that the stem cell preparation in the form of three-dimensional stem cell spheres can provide a safe treatment for arthritis (especially degenerative arthritis). In addition, the current cell therapy products are mostly two-dimensional cells. However, under the two-dimensional culture system, the cell morphology, differentiation, cell-cell interaction, cell-matrix interaction, and in vivo physiological conditions, there are obvious differences. The stem cell preparation of three-dimensional stem cell spheres is used in the present invention for the treatment of arthritis (especially degenerative arthritis). Taking into account the manufacturing specifications of drugs, the closed biological response system and the biological scaffold with three-dimensional porous material can be used to achieve the advantages of sterility, multi-batch, stable production, and the like. It is believed to increase the chance of success and provide new treatment strategies for arthritis (especially degenerative arthritis) in the future.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

According to the present invention, the term "adipose-derived stem cells (ADSCs)" refers to mesenchymal stem cells separated from fat, which are multipotent stem cells having high plasticity. After induction, they can be differentiated into cells of many different tissues.

As used herein, the term "treating" or "treatment" refers to alleviating, reducing, ameliorating, relieving, or controlling one or more clinical signs of a disease or disorder, and lowering, stopping, or reversing the progression of severity regarding the condition or symptom being treated.

According to the present invention, the pharmaceutical composition can be manufactured to a dosage form suitable for parenteral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The pharmaceutical composition according to the present invention may be administered by a parenteral route selected from the group consisting of: intraperitoneal injection, subcutaneous injection, intraepidermal injection, intradermal injection, intramuscular injection, intravenous injection, and intralesional injection.

According to the present invention, the pharmaceutical composition may further comprise a pharmaceutically acceptable carrier which is widely used in pharmaceutically manufacturing techniques. For example, the pharmaceutically acceptable carrier can comprise one or more reagents selected from the group consisting of solvent, emulsifier, suspending agent, decomposer, disintegrating agent, dispersing agent, binding agent, excipient, stabilizing agent, chelating agent, diluent, gelling agent, preservative, lubricant, absorption delaying agent, liposome, and the like. The selection and quantity of these reagents fall within the scope of professionalism and routine techniques of those who are familiar with this technology.

According to the present invention, the pharmaceutically acceptable carrier comprises a solvent selected from the group consisting of water, normal saline, phosphate buffered saline (PBS), sugar-containing solution, aqueous solution containing alcohol, and combinations thereof.

The experimental animals used in the following examples are SD (Sprague-Dawley) male rats. The day before the experiment, the rats to be tested were given a preoperative analgesic injection (ketoprofen, 5 mg/kg), Each rat was first anesthetized with isoflurane, the shaved area was disinfected with iodine, and then 75% alcohol was used for secondary disinfection. 27 G needle was used to inject 50 μL of mono-iodoacetate (MIA) (6 mg/mL) (Sigma, product number A2512) in the left knee joint cavity to induce degenerative arthritis. Sham group was injected with normal saline (50 μL). Ketoprofen (5 mg/kg) would be given daily for postoperative pain relief in three days after surgery.

In the following examples, adipose-derived stem cells (ADSCs) are selected as examples of stem cells. In another example, the stem cells may also be umbilical cord mesenchymal stem cells or a combination of adipose-derived stem cells and umbilical cord mesenchymal stem cells.

In the following examples, degenerative arthritis is selected as an illustration of arthritis. In an example, arthritis may also be arthritis caused by other causes.

Example 1

Preparation and Size of Adipose-Derived Stem Cell (ADSC) Preparations in the Form of Three-Dimensional Stem Cell Spheres The human adipose-derived stem cells (ADSCs) used in the examples of the present invention were obtained from donors during abdominal surgery in accordance with the "Human Cell Therapy Product Donor Eligibility Determination Criteria" issued by the Food and Drug Administration of the Ministry of Health and Welfare. The donors undergo liposuction and 2-5 g of adipose tissue from the subcutaneous fat of the abdominal wall is collected. Written consent was provided by all donors. The human adipose tissue was placed in $Ca^{2+}/Mg^{2+}$-free phosphate buffered saline (PBS) and immediately transferred to the good tissue practice (GTP) laboratory. In the GTP laboratory, human adipose tissue is removed from the transport medium and placed in a petri dish, and cut into small pieces (about 1-2 $mm^3$ in volume) without the presence of $Ca^{2+}/Mg^{2+}$ in PBS. The tissue was dissociated with 0.1% collagenase and incubated at 37° C. for 60 minutes. After collagenase digestion, the resulting cells were collected and cultured in a proliferation medium. The proliferation medium is a serum-free medium, usually a keratinocyte serum-free medium including at least 10% fetal bovine serum, N-acetyl-L-cysteine, L2 ascorbic acid, and phosphate. After culturing for 2 days, the supernatant and debris were removed from the petri dish to obtain primary cultured adipose-derived stem cells.

Next, a two-dimensional cultured stem cell preparation (2D) was prepared as a comparative group. On the day before the animal experiment, two plates of 75T-flask of human primary cultured adipose-derived stem cells (number: 13A001, passage 6) were provided. On the day of the animal experiment, the trypsin solution (containing 0.25% trypsin and EDTA (Sigma, product number: 34549-1 KG) solution, purchased from Gibco, product number: 25200-072) was used to collect cells. After collecting cells, a hemocytometer was used to perform cell counting, and the two-dimensional cultured stem cell preparation was prepared for in vivo injection.

Next, the stem cell preparation in the form of three-dimensional stem cell spheres of the present invention (3D) was prepared as an experimental group. Two plates of 75T-flask of human primary cultured adipose-derived stem cells (number: 13A001, passage 5 and passage 6) were provided, respectively. The trypsin solution was used to collect cells, followed by seeding the cells on the scaffold. The number of seeded cells is at least $1 \times 10^6$ cells/scaffold. In one embodiment of the present invention, the number of seeded cells is $1 \times 10^6$ cells/scaffold. The cell scaffold copolymer was cultured in a 24-well culture plate. After 24 hours of culture to stabilize the cells, the cell scaffold copolymer was transferred to a 50 mL centrifuge tube and a static cultivation was performed for 48 hours. Subsequently, the cell scaffold copolymer was transferred to a bioreactor, and a dynamic cultivation was performed at 37° C., 5% $CO_2$ incubator (Thermo) for 14 days.

Figure 1:
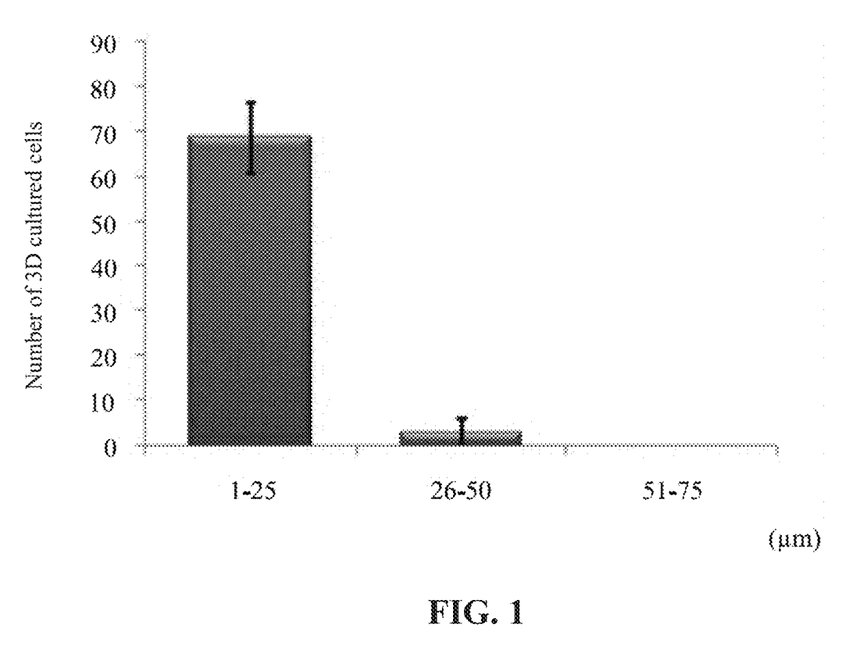
FIG. 1 is a data diagram showing the size of the stem cell preparation in the form of three-dimensional stem cell spheres in the present invention.

After 14 days of dynamic cultivation, the scaffold was dissolved with EDTA/PBS to collect cell spheres, and the size of cell spheres was counted with a cell counter (Automated Brightfield Cell Counter Cellometer® Auto T4). The size of each of the resulting cell spheres is less than 50 μm. The experimental result is shown in FIG. 1.

Example 2

Determination of Cell Number and Dosage of Adipose-Derived Stem Cell Preparation in the Form of Three-Dimensional Stem Cell Spheres A commercially available cell viability detection kit (CellTiter-Glo 3D Cell Viability Assay Kit, Promega, product number: G9682) was used to detect the mitochondrial activity with a known cell number, the average mitochondrial activity of the cells was calculated as a reference standard, and the calculation benchmark value was used to convert the number of cell proliferation after 14 days of dynamic cultivation. The number is $2.35 \times 10^6$ cells/scaffold. This result is used to calculate the number of cells in the cell sphere group in animal experiments.

In addition, the dosages of the two-dimensional cultured cell particles (i.e., the two-dimensional cultured stem cell preparation described in Example 1) and the stem cell preparation in the form of three-dimensional stem cell spheres were found respectively. The dosage of two-dimensional cultured cell particles is as follows. The dosage of cell therapy injected into an animal is $1 \times 10^6$ cells/50 µL, 8 experimental animals in one group, the minimum requirement is $8 \times 10^6$ cells, and the total demand for the experiment is $2 \times 10^7$ cells/mL. The number of cells calculated by hemocytometer ($3.08 \times 10^7$ cells/mL) divided by $2 \times 10^7$ cells/mL is the cell re-dissolution volume of 1.54 mL. 1.54 mL of cell injection provided in this example, with $1.2 \times 10^7$ cells/600 µL, was dispensed into 1 mL syringes (27 G) and provided for subsequent animal experiments (each experimental animal receives 50 µL of cell injection, that is, the cell dose is $1 \times 10^6$ cells/50 µL).

The dosage of the stem cell preparation in the form of three-dimensional stem cell spheres is as follows. The dosage of cell therapy injected into an animal is $1 \times 10^6$ cells/50 µL, 8 experimental animals in one group, the minimum requirement is $8 \times 10^6$ cells, and the total demand for the experiment is $2 \times 10^7$ cells/mL. The number of cells per scaffold is $2.35 \times 10^6$ cells multiplied by 10 scaffolds, the total number of cells is $2.35 \times 10^7$ cells, the total number of cells ($2.35 \times 10^7$ cells) divided by the total demand for the experiment ($2 \times 10^7$ cells/mL) is the cell re-dissolution volume of 1.17 mL. 1.17 mL of cell injection for animal experiments provided in this example, with $1 \times 10^7$ cells/500 µL, was dispensed into 1 mL syringes (27 G) and provided for subsequent animal experiments (each experimental animal receives 50 µL of cell injection, that is, the cell dose is $1 \times 10^6$ cells/50 µL).

Example 3

Result of Gait Analysis of Adipose-Derived Stem Cell Preparation in the Form of Three-Dimensional Stem Cell Spheres on Experimental Animals with Degenerative Arthritis Four groups of experimental animals in this example and the following examples were prepared, including Sham group, mono-iodoacetate (MIA) group, 2D group (i.e. the comparative group) and 3D group (i.e. the experimental group). The treatment methods of each group are shown in Table 1.

TABLE 1

| Group | Sham | MIIA | 2D | 3D |
|---|---|---|---|---|
| MIA | − | + | + | + |
| 2D | − | − | + | − |
| 3D | − | − | − | + |
| Normal saline | + | + | − | − |

Three days after the operation, the rats were anesthetized with isoflurane, and the left knee of each rat was surface-disinfected. The two-dimensional cultured stem cell preparation (2D) ($1 \times 10^6$ cells/50 µL), the stem cell preparation in the form of three-dimensional stem cell spheres (3D) ($1 \times 10^6$ cells/50 µL) and normal saline (50 µL) injected with a 27G needle were injected into the left knee joint cavity of each rat in 2D, 3D and MIA groups respectively. Sham group was injected with normal saline again. A gait analyzer (Clever Sys Inc.) analysis was performed four weeks after the operation.

Figure 2:
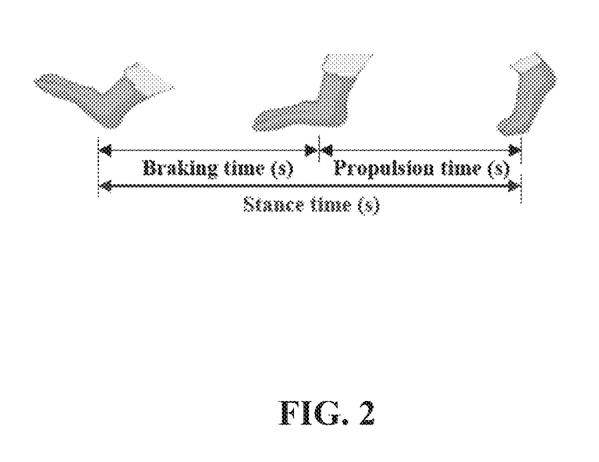
FIG. 2 is a schematic diagram of gait analysis.

The operation flow of gait analysis is as follows. At 4 weeks after the operation of the SD rats, the SD rats were placed on the track of the gait analyzer, and the test was performed at a rate of 23 cm/sec. TreadScan™ 2.0 was used to determine reaction time of the stance, brake and propulsion (see FIG. 2).

Figure 3:
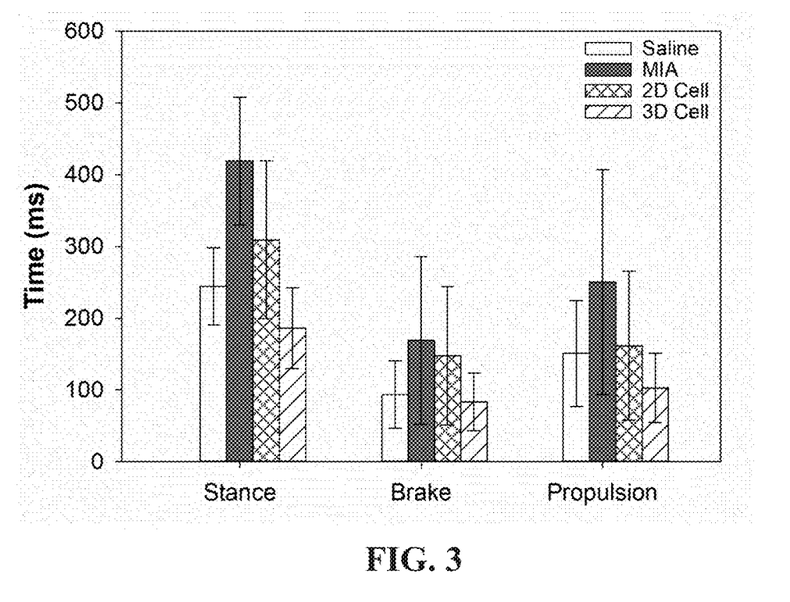
FIG. 3 is a data diagram showing the result of gait analysis of the adipose-derived stem cell preparation in the form of three-dimensional stem cell spheres in the present invention on experimental animals with degenerative arthritis.

The result of gait analysis (see Table 2) confirms that compared with the reaction time of the stance, brake and propulsion of rats in Sham group (without MIA induction and without any treatment), the reaction time of the stance, brake and propulsion of rats induced by MIA without any treatment (MIA group) was increased (see FIG. 3). After 2D and 3D treatment, the reaction time of the stance, brake and propulsion of rats induced by MIA was decreased compared with that of the MIA group. In addition, the reaction time of the 3D group was lower than that of the 2D group, confirming that the stem cell preparation in the form of three-dimensional stem cell spheres of the present invention can indeed improve the walking performance of MIA-induced degenerative arthritis. The gait analysis initially confirms that the prognosis of the 3D group was better than that of the 2D group, in which the stance time was reduced by 39.84%, the brake time was reduced by 43.62%, and the propulsion time was reduced by 36.39%.

TABLE 2

| Time (ms) | Normal saline (Sham) | MIA | 2D | 3D |
|---|---|---|---|---|
| Stance | 244.20 ± 53.71 | 418.88 ± 89.24 | 308.96 ± 110.03 | 185.86 ± 56.35 |
| Brake | 93.43 ± 46.75 | 168.91 ± 116.78 | 147.46 ± 96.26 | 83.14 ± 40.19 |
| propulsion | 150.77 ± 73.77 | 249.96 ± 156.67 | 161.50 ± 103.61 | 102.73 ± 48.04 |

Example 4

Result of Hematoxylin-Eosin (H&E) Staining Regarding Tissue Section of Adipose-Derived Stem Cell Preparation in the Form of Three-Dimensional Stem Cell Spheres on Experimental Animals with Degenerative Arthritis The grouping and treatment of experimental animals are the same as those described in Example 3. The experimental animals in each group were sacrificed at four and eight weeks after the operation, the sampled tissues were immersed and fixed in 10% formaldehyde (Macron) (product number: H121-08) solution for 3 days and then decalcified with 5% nitric acid solution for 2 weeks, followed by replacing with formaldehyde solution. After that, the sampled tissues were sent to the pathology core laboratory of the National Health Research Institutes for dehydration, paraffin embedding and tissue sectioning, and then the paraffin sections were serially stained.

Next, the paraffin sections were deparaffinized with xylene (Sigma) (product number: 534056) and serially rehydrated. The sections were immersed in hematoxylin (Sigma) (product number: GHS3) solution for staining for 5 minutes. The sections were washed in running water for 2 minutes, and then rinsed with deionized water. The sections were immersed in eosin (Sigma) (product number: E4382) solution for staining for 3 minutes. The sections were dehydrated twice with 99% absolute alcohol for 3 minutes each time. The sections were immersed in xylene, and then mounted with mounting medium.

Figure 4:
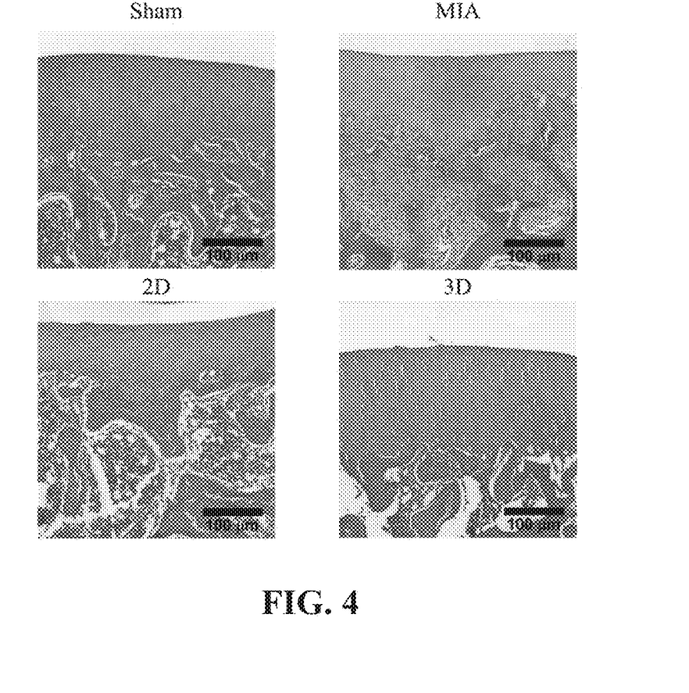
FIG. 4 is a tissue section staining diagram showing the result of hematoxylin-eosin (H&E) staining at 4 weeks after surgery.

The result of H&E staining at 4 weeks after surgery is shown in FIG. 4. It was found in the cartilage section induced by MIA that chondrocytes were destroyed and there were no obvious lacunae in the articular cartilage, proving that degenerative arthritis can be successfully induced with this animal model. Normal cartilage shape was maintained in the Sham group, and chondrocytes were encapsulated in lacunae. It was shown in the sections of rats treated with the two-dimensional cultured stem cell preparation (2D) and the stem cell preparation in the form of three-dimensional stem cell spheres (3D) that the cartilage patterns were more normal compared to those in the MIA group, and there were no significant differences in the cartilage patterns of the 3D group and the Sham group.

Figure 5:
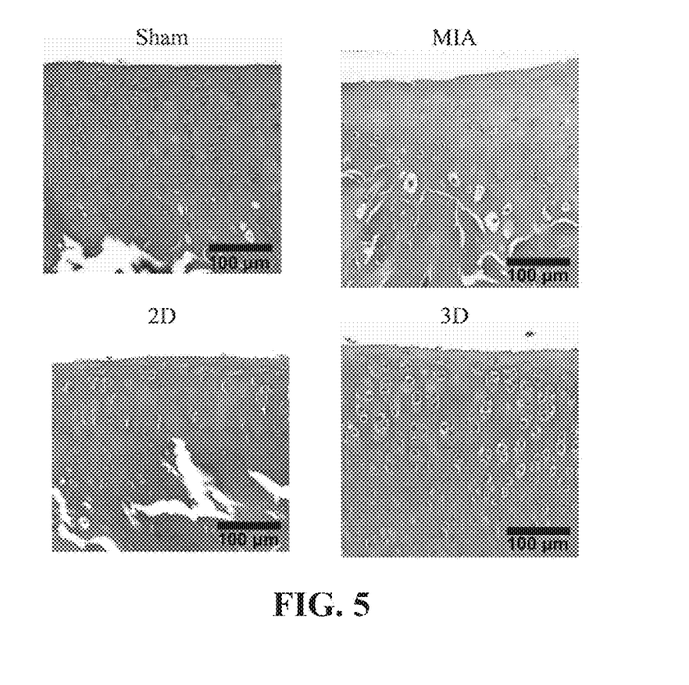
FIG. 5 is a tissue section staining diagram showing the result of hematoxylin-eosin (H&E) staining at 8 weeks after surgery.

The result of H&E staining at 8 weeks after surgery is shown in FIG. 5. The normal cartilage shape was still maintained in the Sham group. However, the cartilages in the MIA group were destroyed. It was shown in the 8 weeks of 2D and 3D treatment that the cartilage type was significantly improved compared with that of the MIA group, and there was no significant difference between the 3D group and the Sham group. The result of H&E staining confirms that the stem cell preparation in the form of three-dimensional stem cell spheres (3D) of the present invention has a better effect of ameliorating degenerative arthritis regardless of whether it is in rats at 4 or 8 weeks.

Example 5

Result of Toluidine Blue Staining Regarding Tissue Section of Adipose-Derived Stem Cell Preparation in the Form of Three-Dimensional Stem Cell Spheres on Experimental Animals with Degenerative Arthritis The grouping and treatment of experimental animals are the same as those described in Example 3. The experimental animals in each group were sacrificed at four and eight weeks after the operation, the sampled tissues were immersed and fixed in 10% formaldehyde (Macron) (product number: H121-08) solution for 3 days and then decalcified with 5% nitric acid solution for 2 weeks, followed by replacing with formaldehyde solution. After that, the sampled tissues were sent to the pathology core laboratory of the National Health Research Institutes for dehydration, paraffin embedding and tissue sectioning, and then the paraffin sections were serially stained.

Next, the paraffin sections were deparaffinized with xylene and rehydrated. The sections were immersed in 0.04% toluidine blue (Sigma) (product number: T3260) solution for staining for 10 minutes. The sections were washed with running water for 1 minute and then allowed to stand for 10 minutes to dry. The sections were immersed in xylene, and then mounted with mounting medium.

Figure 6:
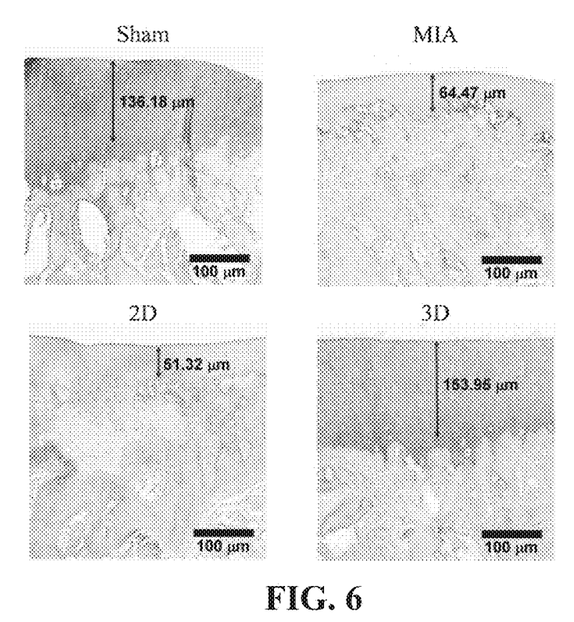
FIG. 6 is a tissue section staining diagram showing the result of toluidine blue staining at 4 weeks after surgery.

The result of toluidine blue staining 4 weeks after surgery is shown in FIG. 6. The length from the cartilage surface to the tidemark is 131.81, 64.47, 51.32 and 153.95 μm in the Sham, MIA, 2D and 3D groups, respectively. The length of the 3D group is increased by 299.98% compared to that of the 2D group. The toluidine blue staining result of the cartilage of rats induced by MIA is negative. The color of the Sham group and the 3D group was toluidine blue positive, and the color of the 2D group was toluidine blue negative.

Figure 7:
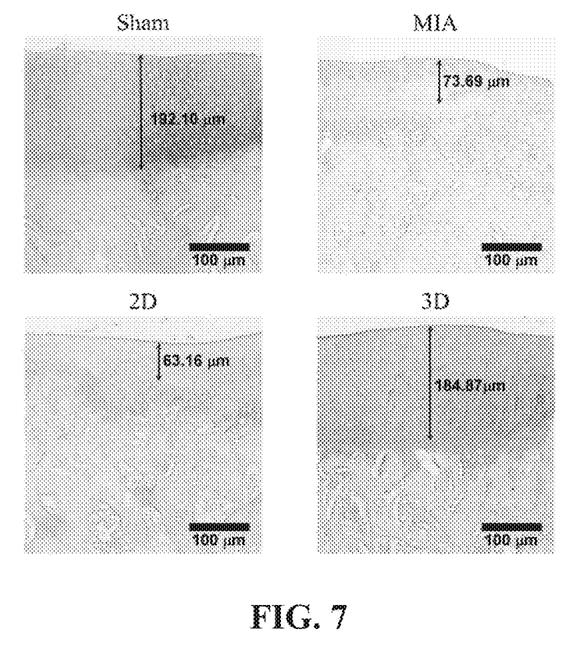
FIG. 7 is a tissue section staining diagram showing the result of toluidine blue staining at 8 weeks after surgery.

The result of toluidine blue staining 8 weeks after surgery is shown in FIG. 7. The length from the cartilage surface to the tidemark is 192.10, 73.69, 63.16 and 184.87 μm in the Sham, MIA, 2D and 3D groups, respectively. The length of the 3D group is increased by 292.7% compared to that of the 2D group. Among them, it was positive for toluidine blue only in the cartilage of the Sham group and the 3D group. The result of toluidine blue staining confirms that the stem cell preparation in the form of three-dimensional stem cell spheres (3D) of the present invention can effectively ameliorate cartilage degeneration caused by degenerative arthritis.

Example 6

Result of Whole Blood Analysis and Blood Biochemical Analysis of Adipose-Derived Stem Cell Preparation in the Form of Three-Dimensional Stem Cell Spheres on Experimental Animals with Degenerative Arthritis The grouping and treatment of experimental animals are the same as those described in Example 3. The experimental animals in each group were collected and sacrificed four weeks and eight weeks after the operation, and the blood was analyzed for whole blood and blood biochemical analysis. Blood samples were obtained from the tail vein at four and eight weeks after the operation, and the whole blood analysis and blood biochemical analysis were performed respectively. The items for whole blood analysis are red blood cell (RBC), white blood cell (WBC), platelet (PLT), monocyte and lymphocyte. The items for blood biochemical analysis items are glutamic oxaloacetic transaminase (GOT), glutamic pyruvic transaminase (GPT), alkaline phosphatase (ALP), blood urea nitrogen (BUN) and creatinine (CRE). The result shows that there was no significant difference between the four-week and eight-week groups (Table 3 to Table 6). This result also confirms that injection of the two-dimensional cultured stem cell preparation (2D) and the stem cell preparation in the form of three-dimensional stem cell spheres of the present invention (3D) into the joint cavity of rats would not cause obvious inflammation and liver and kidney toxicity.

TABLE 3

| | | Whole blood analysis (4 weeks) | | | |
|---|---|---|---|---|---|
| Item | Unit | Sham | MIA | 2D | 3D |
| RBC | $10^6/\mu L$ | 7.67 ± 0.29 | 7.73 ± 0.88 | 7.63 ± 0.51 | 7.63 ± 0.38 |
| WBC | $10^3/\mu L$ | 9.08 ± 0.93 | 9.86 ± 3.39 | 9.92 ± 1.92 | 10.18 ± 0.96 |
| PLT | $10^3/\mu L$ | 866.50 ± 209.56 | 819.50 ± 454.21 | 906.75 ± 391.95 | 911.67 ± 198.61 |
| monocyte | $10^3/\mu L$ | 0.46 ± 0.10 | 0.41 ± 0.14 | 0.45 ± 0.10 | 0.49 ± 0.07 |
| lymphocyte | $10^3/\mu L$ | 6.53 ± 0.65 | 6.61 ± 3.03 | 5.96 ± 2.04 | 7.15 ± 0.47 |

TABLE 4

| | | Blood biochemical analysis (4 weeks) | | | |
|---|---|---|---|---|---|
| Item | Unit | Sham | MIA | 2D | 3D |
| GOT | U/L | 88.33 ± 9.29 | 110.00 ± 1.41 | 108.50 ± 2.12 | 87.50 ± 7.78 |
| GPT | U/L | 28.75 ± 2.22 | 35.75 ± 5.74 | 34.00 ± 3.46 | 30.00 ± 4.40 |
| ALP | U/L | 1127.50 ± 428.25 | 1085.00 ± 268.52 | 1082.75 ± 224.38 | 1055.00 ± 344.34 |
| BUN | mg/dL | 17.75 ± 2.00 | 19.80 ± 1.42 | 19.75 ± 1.42 | 18.65 ± 2.51 |
| CRE | mg/dL | 0.34 ± 0.04 | 0.28 ± 0.02 | 0.25 ± 0.03 | 0.28 ± 0.05 |

TABLE 5

| | | Whole blood analysis (8 weeks) | | | |
|---|---|---|---|---|---|
| Item | Unit | Sham | MIA | 2D | 3D |
| RBC | $10^6/\mu L$ | 8.11 ± 0.54 | 7.98 ± 0,59 | 7.99 ± 0.22 | 8.32 ± 0.44 |
| WBC | $10^3/\mu L$ | 6.36 ± 1.50 | 6.76 ± 0.88 | 6.65 ± 0.49 | 6.54 ± 0.75 |
| PLT | $10^3/\mu L$ | 943.50 ± 67.18 | 939.33 ± 273.35 | 937.33 ± 290.18 | 868.50 ± 62.66 |
| monocyte | $10^3/\mu L$ | 0.41 ± 0.09 | 0.32 ± 0.09 | 0.37 ± 0.11 | 0.39 ± 0.05 |
| lymphocyte | $10^3/\mu L$ | 4.48 ± 0.86 | 4.03 ± 0.66 | 4.17 ± 0.52 | 4.19 ± 0.46 |

TABLE 6

| | | Blood biochemical analysis (8 weeks) | | | |
|---|---|---|---|---|---|
| Item | Unit | Sham | MIA | 2D | 3D |
| GOT | U/L | 71.25 ± 3.40 | 67.50 ± 21,02 | 81.50 ± 19.84 | 83.50 ± 6.36 |
| GPT | U/L | 27.70 ± 2.38 | 27.75 ± 6.29 | 27.50 ± 5.92 | 32.50 ± 1.00 |
| ALP | U/L | 890.50 ± 53.03 | 850.67 ± 154.57 | 877.00 ± 150.79 | 928.00 ± 64.63 |
| BUN | mg/dL | 18.40 ± 1.14 | 19.33 ± 3.44 | 19.27 ± 4.10 | 18.20 ± 0.84 |
| CRE | mg/dL | 0.23 ± 0.02 | 0.28 ± 0.03 | 0.27 ± 0.04 | 0.26 ± 0.03 |

Example 7

OA Score of Adipose-Derived Stem Cell Preparation in the Form of Three-Dimensional Stem Cell Spheres on Experimental Animals with Degenerative Arthritis The grouping and treatment of experimental animals are the same as those described in Example 3. The experimental animals in each group were sacrificed at four and eight weeks after the operation, the sampled tissues were immersed and fixed in 10% formaldehyde (Macron) (product number: H121-08) solution for 3 days and then decalcified with 5% nitric acid solution for 2 weeks, followed by replacing with formaldehyde solution. After that, the sampled tissues were sent to the pathology core laboratory of the National Health Research Institutes for dehydration, paraffin embedding and tissue sectioning, and then the paraffin sections were serially stained.

Next, the paraffin sections were deparaffinized with xylene and rehydrated. The sections were immersed in 0.04% toluidine blue (Sigma) (product number: T3260) solution for staining for 10 minutes. The sections were washed with running water for 1 minute and then allowed to stand for 10 minutes to dry. The sections were immersed in xylene, and then mounted with mounting medium.

Toluidine blue stained sections were scored for degenerative arthritis according to the scoring method disclosed by the Osteoarthritis Research Society International, and the score is the product of Grade×Stage.

Figure 8:
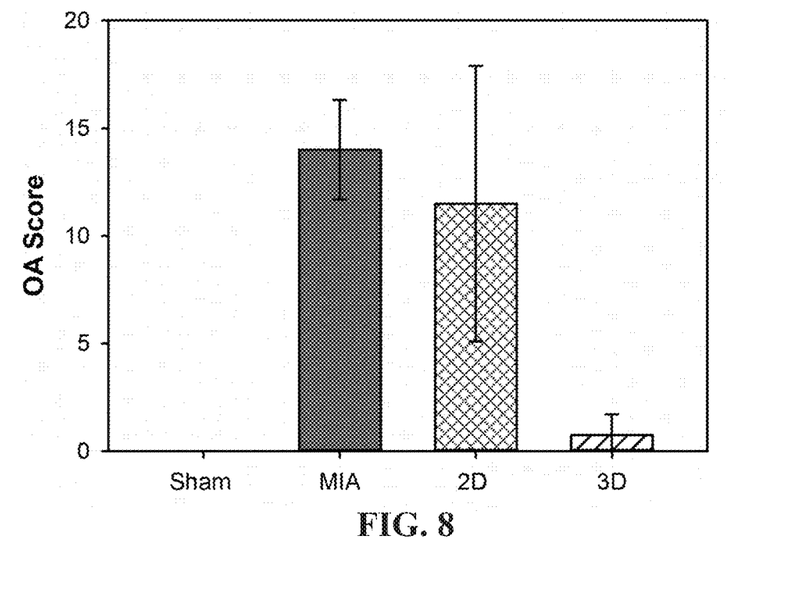
FIG. 8 is a data diagram showing the result of the osteoarthritis (OA) score of the adipose-derived stem cell preparation in the form of three-dimensional stem cell spheres in the present invention on experimental animals with degenerative arthritis four weeks after surgery.
Figure 9:
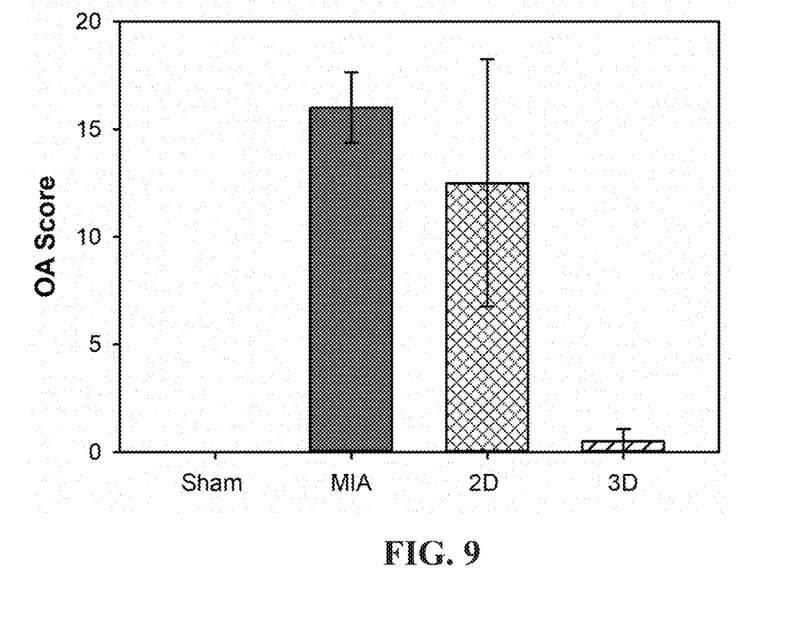
FIG. 9 is a data diagram showing the result of the osteoarthritis (OA) score of the adipose-derived stem cell preparation in the form of three-dimensional stem cell spheres in the present invention on experimental animals with degenerative arthritis 8 weeks after surgery.

Four weeks and eight weeks of toluidine blue stained sections were evaluated for degenerative arthritis score. The scores at four weeks after surgery are 0±0, 14±2.31, 11.5±6.40 and 0.75±0.96 in the Sham, MIA, 2D and 3D groups, respectively (FIG. 8). The scores at eight weeks after surgery are 0±0, 16±1.63, 12.5±5.74 and 0.5±0.57 in the Sham, MIA, 2D and 3D groups, respectively (FIG. 9). The result of this example shows that the adipose-derived stem cell preparation in the form of three-dimensional stem cell spheres of the present invention can effectively ameliorate degenerative arthritis.

Example 8

Cartilage-Related Gene Expression of Stem Cell Preparation in the Form of Three-Dimensional Stem Cell Spheres The human umbilical cord mesenchymal stem cells (Wharton's jelly) used in this example were purchased from the Bioresource Collection and Research Center (BCRC) of the Food Industry Research and Development Institute.

Human adipose-derived stem cells (hADSCs) and human umbilical cord mesenchymal stem cells were prepared according to the preparation method in Example 1. After 14 days of culture, the mRNAs of the cells were isolated using an mRNA isolation kit (Quick-RNAIM MiniPrep, ZYMO RESEARCH), and reverse-transcribed into cDNA using a reverse transcription kit (PrimeScript™ RT reagent Kit, Takara). SYBR® Premix Ex Taq™ II (Takara) was used to mix 100 ng of cDNA samples and appropriate primers for the transforming growth factor β1 (TGF-β1) gene, the bone morphogenetic protein-2 (BMP-2) gene, the Sox9 gene, the Aggrecan gene, the cartilage oligomeric matrix protein (COMP) gene, and the Collagen, type II, alpha 1 (Col2a1) gene were selected for real-time polymerase chain reaction (real-time PCR). The primer sequence of each gene is shown in Table 7.

TABLE 7

| Gene name | | | SEQ ID NO |
|---|---|---|---|
| TGF-β1 | Forward | GGT TGA GCC GTG GAG GGG AAA T | SEQ ID NO: 1 |
| | Reverse | TGC CAT GAA TGG TGG CCA GGT | SEQ ID NO: 2 |
| BMP-2 | Forward | CGC TGT CTT CTA GCG TTG C | SEQ ID NO: 3 |
| | Reverse | TCG TCA GAG GGC TGG GAT G | SEQ ID NO: 4 |
| Sox9 | Forward | GGC AAG CTC TGG AGA CTT CTG | SEQ ID NO: 5 |
| | Reverse | CTG CAG CGC CTT GAA GAT G | SEQ ID NO: 6 |
| Aggrecan | Forward | TCG AGG ACA GCG AGG CC | SEQ ID NO: 7 |
| | Reverse | TCG AGG GTG TAG CGT GTA GAG A | SEQ ID NO: 8 |
| COMP | Forward | ACA ATG ACG GAG TCC CTG AC | SEQ ID NO: 9 |
| | Reverse | TCT GCA TCA AAG TCG TCC TG | SEQ ID NO: 10 |
| Col2a1 | Forward | GAG ACA GCA TGA CGC CGA G | SEQ ID NO: 11 |
| | Reverse | GCG GAT GCT CTC AAT CTG GT | SEQ ID NO: 12 |
| GAPDH | Forward | TGC CCC CGA CCG TCT AC | SEQ ID NO: 13 |
| | Reverse | ATG CGG TTC CAG CCT ATC TG | SEQ ID NO: 14 |

After the mRNAs isolation of the adipose-derived stem cell preparation in the form of three-dimensional stem cell spheres prepared in Example 1, the mRNAs were reverse transcribed into cDNAs, and real-time PCR was performed. The expression level of each gene was analyzed and recorded, as shown in Table 8 and FIG. 10. Table 8 and FIG. 10 show the expression level of mRNA in the cells after human adipose-derived stem cells (hADSCs) have been cultured in two (2D) and three dimensions (3D) (that is, the adipose-derived stem cell preparation in the form of three-dimensional stem cell spheres in the present invention) on day 14.

TABLE 8

| Relative mRNA Expression | 2D | 3D |
|---|---|---|
| TGF-β1 | 1 | 2.43 ± 0.03 |
| BMP-2 | 1 | 20.84 ± 5.76 |
| Sox9 | 1 | 8.14 ± 1.37 |
| Aggrecan | 1 | 4.52 ± 1.53 |
| COMP | 1 | 23.85 ± 10.21 |
| Col2a1 | 1 | 23.76 ± 7.74 |

Figure 10:
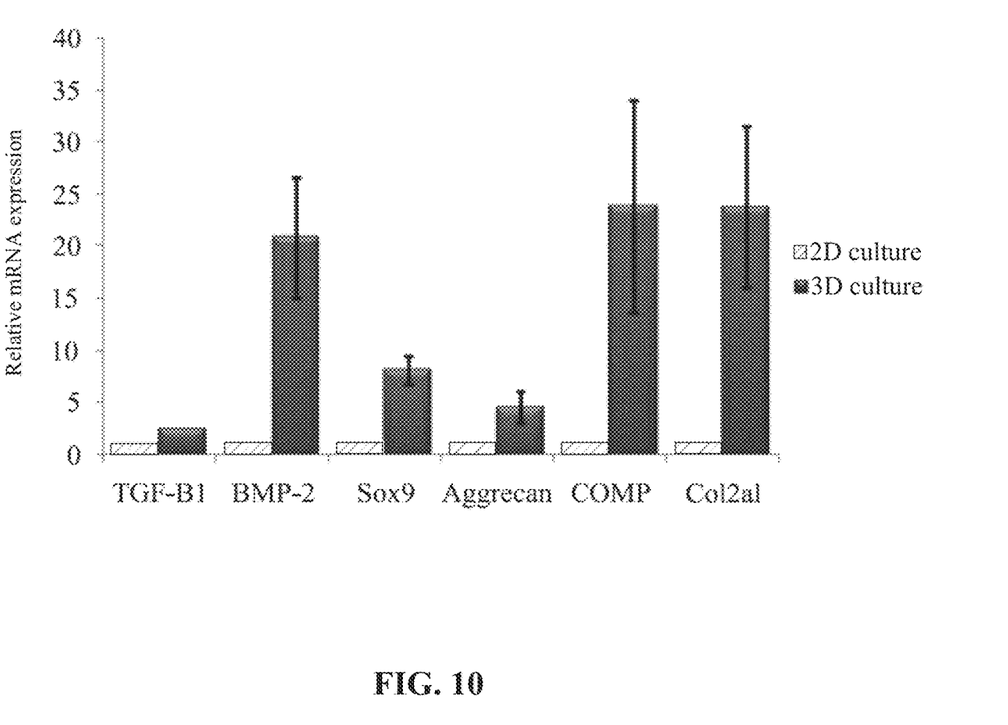
FIG. 10 is a data diagram showing that after human adipose-derived stem cells (hADSCs) have been cultured in two and three dimensions (that is, the adipose-derived stem cell preparation in the form of three-dimensional stem cell spheres in the present invention) on day 14, the expression level of mRNA in the cells.

As shown in Table 8 and FIG. 10, the expression levels of the TGF-β1 gene, the BMP-2 gene, the Sox9 gene, the Aggrecan gene, the COMP gene and the Col2a1 gene in the three-dimensional cultured cells of hADSC after 14 days of culture are significantly increased compared to those of the two-dimensional cultured cells. The range of increase is about 2 to 25 times.

Figure 11A:
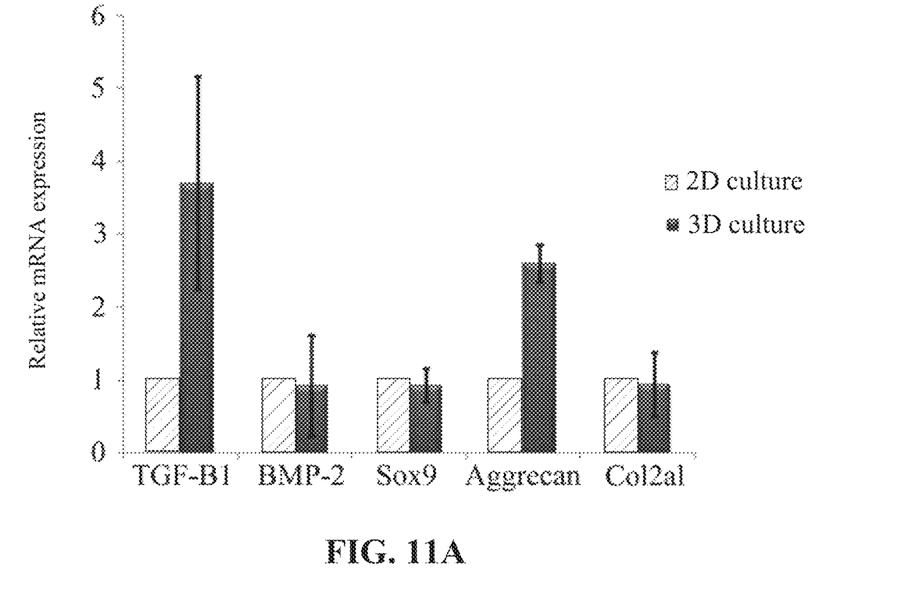
FIG. 11A is a data diagram showing that after human umbilical cord mesenchymal stem cells have been cultured in two and three dimensions (that is, the stem cell preparation in the form of three-dimensional stem cell spheres in the present invention prepared by referring to the method described in Example 1) on day 14, the expression level of mRNA in the cells.
Figure 11B:
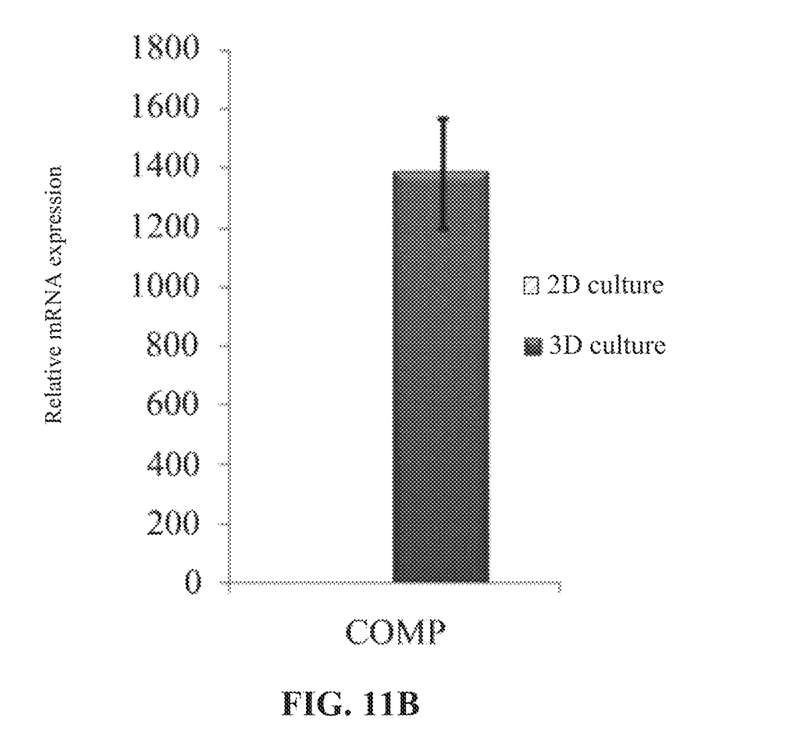
FIG. 11B is a data diagram showing that after human umbilical cord mesenchymal stem cells have been cultured in two and three dimensions (that is, the stem cell preparation in the form of three-dimensional stem cell spheres in the present invention prepared by referring to the method described in Example 1) on day 14, the expression level of mRNA in the cells.

Table 9, FIG. 11A and FIG. 11B show the expression level of mRNA in the cells after human umbilical cord mesenchymal stem cells have been cultured in two (2D) and three dimensions (3D) (that is, the stem cell preparation in the form of three-dimensional stem cell spheres in the present invention prepared by referring to the method described in Example 1) on day 14. The mRNA expression of the 2D group is taken as 1, and the relative mRNA expression is calculated. It should be noted that in FIG. 11B, due to the large difference in the relative mRNA expressions between the two groups and the widening of the Y-axis spacing, the mRNA expressions of the 2D group cannot be clearly displayed, but it does not mean that there is no COMP gene expression in the 2D group.

TABLE 9

| Relative mRNA Expression | 2D | 3D |
|---|---|---|
| TGF-β1 | 1 | 3.70 ± 1.47 |
| BMP-2 | 1 | 0.9 ± 0.7 |
| Sox9 | 1 | 0.9 ± 0.22 |
| Aggrecan | 1 | 2.6 ± 0.25 |
| COMP | 1 | 1386 ± 186 |
| Col2a1 | 1 | 0.9 ± 0.43 |

As shown in Table 9, FIG. 11A and FIG. 11B, the expression levels of the TGF-β1 gene, the Aggrecan gene, and the COMP gene in the three-dimensional cultured human umbilical cord mesenchymal stem cells after 14 days of culture are significantly increased compared to those of the two-dimensional cultured cells. The range of increase is about 2.4 to 1572 times.

In summary, the effect of the stem cell preparation of the present invention is that treating rats with arthritis induced by mono-iodoacetate (MIA), using a gait analyzer and hematoxylin & eosin (H&E) staining and toluidine blue staining for treatment evaluation, and evaluating the feasibility of applying the stem cell preparation to the treatment of arthritis. It was found that the stem cell preparation of the present invention can effectively delay arthritis (especially degenerative arthritis) caused by cartilage degradation, and whole blood analysis and blood biochemical analysis confirmed that the stem cell preparation in the form of three-dimensional stem cell spheres can provide a safe treatment for arthritis (especially degenerative arthritis). In addition, the current cell therapy products are mostly two-dimensional cells. However, under the two-dimensional culture system, the cell morphology, differentiation, cell-cell interaction, cell-matrix interaction, and in vivo physiological conditions, there are obvious differences. The stem cell preparation of three-dimensional stem cell spheres is used in the present invention for the treatment of arthritis (especially degenerative arthritis). Taking into account the manufacturing specifications of drugs, the closed biological response system and the biological scaffold with three-dimensional porous material can be used to achieve the advantages of sterility, multi-batch, stable production, and the like. It is believed to increase the chance of success and provide new treatment strategies for arthritis (especially degenerative arthritis) in the future.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for treating arthritis, comprising administering to a subject in need thereof a pharmaceutical composition comprising an effective amount of a stem cell preparation, wherein the stem cell preparation comprises a stem cell sphere, wherein:
   the stem cell sphere has a size greater than 0 μm and less than 50 μm;
   the stem cell sphere comprises a stem cell selected from the group consisting of an adipose-derived stem cell (ADSC), an umbilical cord mesenchymal stem cell, and a combination thereof; and
   the stem cell sphere expresses a cartilage-related gene selected from the group consisting of a transforming growth factor-β1 (TGF-β1) gene, a bone morphogenetic protein-2 (BMP-2) gene, a Sox9 gene, an Aggrecan gene, a collagen type II alpha 1 chain (Col2a1) gene, and a combination thereof;
   wherein the stem cell sphere is prepared by seeding the adipose-derived stem cell, the umbilical cord mesenchymal stem cell, or a combination thereof on a scaffold to form a cell scaffold copolymer, followed by sequentially performing a static cultivation for a period of about 48 hours and a dynamic cultivation for a period of about 14 days on said cell scaffold copolymer;
   wherein the adipose-derived stem cell, the umbilical cord mesenchymal stem cell, or a combination thereof is seeded on the scaffold at a concentration of $1\times10^6$ cells/scaffold; and
   wherein administration of the stem cell preparation increases cartilage thickness.

2. The method according to claim 1, wherein the arthritis is degenerative arthritis.

3. The method according to claim 1, wherein the adipose-derived stem cell is a human adipose-derived stem cell.

4. The method according to claim 1, wherein the stem cell preparation has a concentration of $1\times10^6$ cells/50 μL.

5. The method according to claim 1, wherein the stem cell sphere expresses a surface marker selected from the group consisting of: CD73, CD90, CD105, and a combination thereof.

6. The method according to claim 1, wherein the pharmaceutical composition is in a dosage form for parenteral administration.

* * * * *